United States Patent
Kruchinin et al.

[11] Patent Number: 6,036,716
[45] Date of Patent: Mar. 14, 2000

[54] MICRO-SURGERY FIXATION DEVICE, VARIANTS MANIPULATION PUSH-BAR FOR MOUNTING THE SAME

[76] Inventors: Boris Petrovich Kruchinin, 121609 Rublevskoye shosse, d.28, korp.3, kv.208; Vladimir Leonidovich Karpenko, 113186 ul.Nagornaya, d.29, korp.2, kv.67, both of Moscow, Russian Federation

[21] Appl. No.: 09/214,670
[22] PCT Filed: Jun. 27, 1997
[86] PCT No.: PCT/RU97/00199
§ 371 Date: Jan. 8, 1999
§ 102(e) Date: Jan. 8, 1999
[87] PCT Pub. No.: WO98/01086
PCT Pub. Date: Jan. 15, 1998

[30] Foreign Application Priority Data

Jul. 9, 1996 [RU] Russian Federation ............. 96114370

[51] Int. Cl.⁷ ............................ A61M 29/00; A61M 5/32
[52] U.S. Cl. ...................... 606/198; 606/191; 604/104; 604/107
[58] Field of Search ................... 606/198, 1, 108, 606/191, 200; 604/104–109, 280, 282; 623/1; 600/206

[56] References Cited

U.S. PATENT DOCUMENTS

| | | | |
|---|---|---|---|
| 4,580,568 | 4/1986 | Gianturco | 604/96 |
| 4,817,587 | 4/1989 | Janese | 600/206 |
| 5,035,706 | 7/1991 | Gianturco et al. | 606/198 |
| 5,279,564 | 1/1994 | Taylor | 604/104 |
| 5,383,887 | 1/1995 | Nadal | 606/200 |
| 5,507,771 | 4/1996 | Gianturo | 606/198 |
| 5,855,565 | 1/1999 | Bar-Cohen et al. | 604/104 |
| 5,922,020 | 7/1999 | Klein et al. | 623/1 |
| 5,925,061 | 7/1999 | Ogi et al. | 606/198 |

*Primary Examiner*—Gary Jackson
*Attorney, Agent, or Firm*—Collard & Roe, P.C.

[57] ABSTRACT

The present invention relates to medicine, more specifically to microsurgery and can find application both for dilating stenosed portions of tubular organs and blood vessels and for fixing the edges of holes in tissues or holding prostheses, e.g., when positioning occluding, valve, or filtering prosthetic appliances on parietal lesions or defects, as well as on inosculations of hollow or tubular organs. The invention makes possible extending the field of application and functional capabilities of the microsurgical fixing device, as well as to enhance its reliability and safety of its positioning. According to one of its embodiments the microsurgical fixing device appears as at least two springs each appearing as a cone frustum or a flat ring made from a Z-shaped bar that forms a closed loop. The springs are movably interconnected through the apices of zigzags which are situated on the same circle so as to provide reversible compression of the springs under the effect of external load. In an alternative embodiment of the invention the microsurgical fixing device comprises a single spring appearing as a cone frustum or a flat ring made from a Z-shaped bar forming a closed loop. The zigzag apices lying on the same circle are provided with retainers movably connected thereto, each appearing as an elastic bar provided with a hook. The manipulation pusher appears as a number of tie-members provided with slideways connected, through a coupling, to a guide-catheter. The tie-members are accommodated in the coupling and the guide-catheter longitudinally movably thereinside and with respect to the slideways.

34 Claims, 4 Drawing Sheets

MICRO-SURGERY FIXATION DEVICE, VARIANTS MANIPULATION PUSH-BAR FOR MOUNTING THE SAME

TECHNICAL FIELD

The present invention relates in general to medicine and more specifically to microsurgery; the invention can find application both for dilating stenosed portions of tubular organs and blood vessels and for fixing the edges of holes in tissues or holding prostheses, e.g., when positioning occluding, valve, or filtering prosthetic appliances on parietal lesions or defects, as well as on inosculations of hollow or tubular organs.

BACKGROUND ART

Known in the present state of the art is a microsurgery fixing member of a self-locking vascular prosthesis (cf. USSR Inventor's Certificate # 1,217,402, IPC A61F 2/06, 1986), which is in fact a flat spring appearing as a wire bent into a Z-shape. However, the device in question is inconvenient in use, since the spring fails to establish a closed loop or circuit.

Another disadvantage of the fixing member under discussion resides in that its field of application is limited only to fixing a prosthetic vessel. One prior-art microsurgery fixing device (U.S. Pat. No. 4,580,568, IPC A61M 1/34, 1986) is known to appear as a spring bent into a Z-shape establishing a closed loop or circuit formed as a cylinder.

The known device is disadvantageous in that its field of application is limited and the device is applicable only to hollow tubular organs. A prior-art device for installing a self-locking vascular prosthesis (cf. USSR Inventor's Certificate # 1,318,235, IPC A61M 29/00, 1986) is known to comprise a flexible tubular guide and a pusher, both enabling the prosthesis to be transported and positioned in the lumen of the vessel involved. The aforementioned known positioning means is disadvantageous in that it is incapable of changing the position of the prosthesis after the latter has been released from the tubular guide.

A prior-art manipulation device for positioning an intravenous filter (cf. RU Patent # 2,000,18, IPC A61M 1/34, 1992) is known to comprise a pusher appearing as a stilet with tie-members held in place thereto and appearing as elastic bars provided with coupling sleeves fixed at their ends and aimed at joining with the appliance being implanted.

A disadvantage inherent in said known positioner resides in that its construction does not provide a possibility of withdrawing the implantable appliance. In addition, its use is fraught with a danger of a premature disjoining from the fixing members of the appliance being implanted.

DISCLOSURE OF THE INVENTION

With specific problem in mind, it is a particular and primary object of the present invention, as far as the microsurgical fixing device is concerned, to extend the field of application and functional capabilities of the proposed microsurgical fixing device, namely, to provide a possibility of strengthening the edges of holes in tissues and fixing occluding, valve, or filtering prosthetic appliances on parietal defects or on inosculations of hollow or tubular organs.

With specific problem in mind, it is a particular and primary object of the present invention, as far as the manipulation positioning pusher is concerned, to attain higher reliability and safety in positioning the fixing device by providing a possibility to position, remove, displace, or withdraw it while neither breaking the device nor damaging the surrounding tissues. The foregoing object is accomplished, as far as the microsurgical fixing device is concerned, due to the fact that said device comprising a spring appearing as an elastic Z-shaped bar that forms a closed loop, further comprises at least one spring appearing also as an elastic Z-shaped bar, each of said springs being so arranged that its opposing apices are disposed along the perimeters of the bases of a cone frustum or along concentric circles that form a flat ring, while the apices of zigzags of said Z-shaped bar in each spring located on the same base of the cone frustum or along the same ring circle are joined together with the apices of zigzags of a next spring which are also arranged on the same base of the cone frustum or along the same ring circle through joining members so as to provide a possibility for said springs to be compressed reversibly, and the apices of zigzags not joined together are adapted to receive the actuating members of a positioning unit.

In a specific embodiment of the proposed microsurgical device it comprises two springs, each appearing as a cone frustum, while joined together are the apices of zigzags located on the greater bases of the cone frustums formed by each of the springs.

In another specific embodiment of the proposed microsurgical device it comprises two springs, each appearing as a cone frustum, while joined together are the apices of zigzags located on the lesser bases of the cone frustums formed by each of the springs.

The springs are in this case put together with the greater bases of the cone frustums.

In particular, the diameters of the greater bases of the cone frustums formed by each spring are unequal. In specific embodiments of the device angles at the greater bases of the cone frustums formed by each spring, are not in excess of 45 degrees, which provides for a permissible pressure exerted by the springs upon the tissues. Furthermore, with a view to increasing spring stiffness, at least one spring turn is provided at each zigzag apex.

In a specific embodiment of the proposed device the bar from which the spring is manufactured is made of wire having its various portions differing in shape and cross-sectional area.

In a specific embodiment of the proposed device each joining member appears as a bracing ring whose size is selected so that the device may be placed in the positioning unit.

Specifically, the bracing ring appears as at least single spring turn. Furthermore, with a view to make possible putting patches on rather thick tissues, or strengthening the edges of such a tissue, each joining member appears as an elastic bar provided with rings or holes at its ends, the size of said rings being so selected that the device may be placed in the positioning unit.

Specifically, each joining member is made of wire and appears as a tension spring provided with rings at its ends, the size of said rings being so selected that the device may be placed in the positioning unit.

The foregoing object is accomplished also due to the fact that in a microsurgical fixing device, comprising a spring appearing as an elastic Z-shaped bar that forms a closed loop, said spring is so arranged that its opposing apices are arranged along the perimeters of the bases of a cone frustum or along concentric circles which form a flat ring, while all the apices of Z-shapes that are located on one of the bases of the cone frustum or on one of the circles of said flat ring are provided with retainers each of which appears as an elastic bar and has at least one hook; each retainer is movably connected, through the joining members, to one or two apices of zigzags so as to provide reversible compression of the spring; all the retainers are situated on the same side of the spring and the free ends of the retainer bars are adapted to receive the actuating members of the positioning unit.

Furthermore, the angle at the greater base of a cone frustum defined by the spring, is not in excess of 45 degrees, which provides for a permissible pressure exerted by the springs upon the tissues. Furthermore, the hooks of all the retainers are oriented away from the spring axis.

Furthermore, with a view to increasing the spring stiffness, at least one spring turn is provided at each of the zigzag apices. In a specific embodiment of the proposed device the bar from which the spring is manufactured, is made of wire having its various portions differing in shape and cross-sectional area and is provided with hooks, or knurling, or spring turns.

Furthermore, a hole or ring is provided at the end of each retainer opposite to the free end thereof for movably connecting the retainer to the joining member.

In a specific embodiment of the device each joining member connecting the retainer to one zigzag apex appears as a closed ring or a ring with at least one spring turn, the size of said rings being so selected that the device may be placed in the positioning unit.

In an another specific embodiment of the device each joining member is made from an elastic bar and appears as a symmetrically curved clip having a back and two legs provided with rings at their ends and connected to two adjacent zigzag apices, while the clip back is connected to the retainer. Specifically, the clip back has at least one spring turn.

Furthermore, in order to accomplish the aforesaid object, each retainer has the free end of its bar adapted to receive the actuating members of the positioning unit, is provided with a hole, or ring, or projection, or recess. In a specific embodiment of the invention the retainer hook is fitted on a sleeve fixed in position on the retainer bar.

In an another specific embodiment of the invention the retainer hook is provided on a sleeve which is movable over the retainer bar from the initial to the fixing position.

Furthermore, with a view to more reliably fixing the device on tissues, each joining member has at least one further hook. The foregoing object is attained, as far as the manipulation positioning pusher is concerned, due to the fact that the pusher comprising a number of tie-members each of which is adapted to be joined with the components of the present microsurgical device, further comprises slideways in a number equal to that of the tie-members, and a guide-catheter connected, through a coupling, to the slideways secured thereon; each tie-member is longitudinally movable inside the coupling and the guide-catheter with regard to its respective slideway, the length of each tie-member exceeds a total length of its respective slideway, the coupling, and the guide-catheter; the distal end of each slideway is adapted to interact with the component of the microsurgery device joined with the corresponding tie-member and the guide-catheter carries a clamping fixture adapted to fix the tie-members in position.

In a specific embodiment of the invention each tie-member is made of a loop-shaped flexible cord or string.

In an another specific embodiment of the invention the tie-members appear as elastic bars provided with hooks, or projections, or recesses at the ends thereof which deflect at a maximum angle of 90 degrees with respect to the axis of the manipulation pusher.

In a specific embodiment of the invention the slideways appear as small flexible tubes inside which tie-members are accommodated. In a specific embodiment of the invention the slideways appear as small tubes inside which tie-members are accommodated and which are secured on the coupling through elastic bars that deflect at a maximum angle of 90 degrees with respect to the axis of the manipulation pusher.

In some specific embodiments of the invention the slideways are equal in length.

In a specific embodiment of the invention the coupling is fitted at the distal end of the guide-catheter.

In an another specific embodiment of the invention the coupling is fitted at the proximal end of the guide-catheter through an articulated joint and the slideways are accommodated inside the guide-catheter and extend beyond its distal end.

Furthermore, with a view to avoiding deformation of the retainer hooks and ensuring against injury to the surrounding tissues when positioning the present fixing device, it further comprises a safeguarding tube fitted on the guide-catheter coaxially therewith.

BRIEF DESCRIPTION OF THE DRAWINGS

In what follows the present invention is explained in the disclosure of exemplary embodiments thereof given by way of illustration to be taken in conjunction with the accompanying drawings, wherein.

MODES OF CARRYING OUT THE INVENTION

The microsurgical fixing device comprises one or more springs 1 (in the various variants of the device) which are made from an elastic Z-shaped bar that forms a closed loop by joining together the free ends of said elastic bar. Provision may be made on the elastic Z-shaped bar of the spring for hooks, clips, knurling, or spring turns for holding the spring on tissue and securing the prosthetic appliance on the spring.

Figure 1:
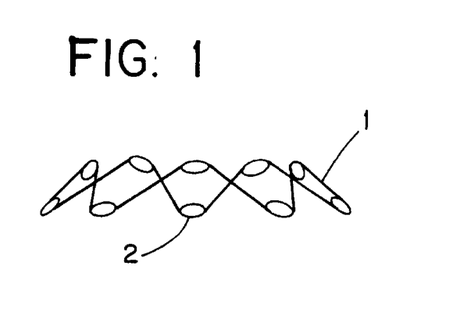
FIG. 1 is a side view of a spring of the microsurgical fixing device, according to the invention.
Figure 2:
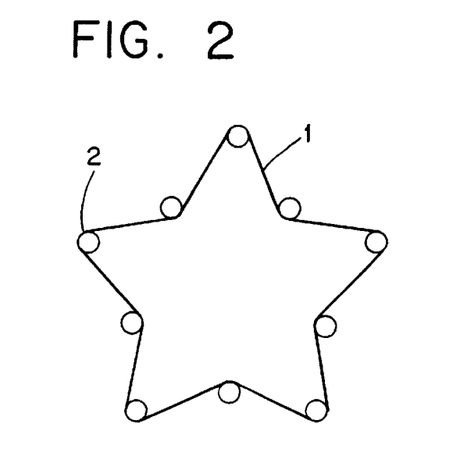
FIG. 2 is a plan view of the spring of the microsurgical fixing device, according to the invention.
Figure 3:
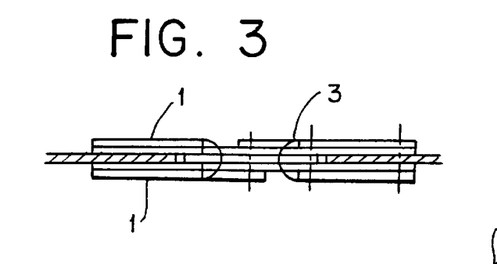
FIGS. 3 and 4 present a sectional view of the microsurgical fixing device while positioned on tissues, comprising two springs interconnected through the various joining members, according to the invention.
Figure 4:
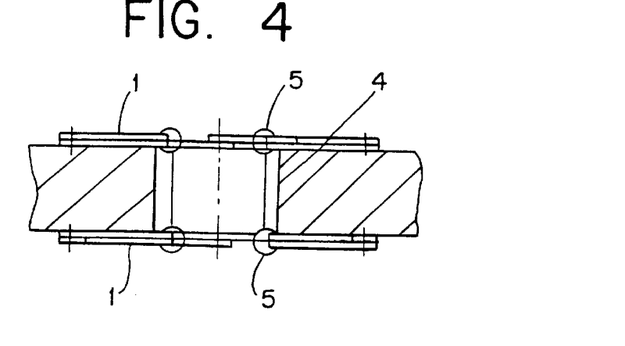

Each spring is so arranged that opposing apices of the zigzags of the elastic bar are inscribed in different-diameter circles whose centers are arranged on the same axis square with each of said circles. The circles in question may be both coplanar and noncoplanar. Exemplified in FIG. 1 is a spring shaped as a cone frustum. The spring may also be so arranged that the bar portions between the apices of zigzags are arcuate in shape, and the bar bents are directed away from the axis of symmetry of the spring. One or more spring turns 2 may be established in each zigzag apex. In one of the embodiments of the present invention use is made of two interconnected springs (FIGS. 3 and 4).

The springs 1 are interconnected through joining members appearing as bracing rings 3 both closed and comprising one or more spring turns, and as an elastic bar 4 provided with rings 5 or holes at its ends, or else as a tension spring having rings at its ends. When the present device is to be positioned on rather thick tissues, use is made of the joining members in the form of an elastic bar or a tension spring.

The joining members are so made as to provide an unobstructed reversible compression of the springs within a cylindrical interior space of the positioning unit.

The microsurgical fixing device may comprise two or more springs of any configuration proposed herein, put together in any possible combination. Specifically, the springs present in FIGS. 3 and 4 may be put together with the greater bases of cone frustums, and the joining members interconnect the spring apices located on the lesser base of the cone frustum. Once joined together the springs acquire a flat shape (ring) and appear to be in a slightly loaded state, whereby the device is fixed on tissues more reliably. A reliable fixing of the device on tissues is attained also when use is made of springs featuring a very small angle at the base of cone frustum, as well as with the springs appearing as flat rings, this being due to the fact that at any possible load arising during operation the springs encompass snugly the edges of a hole in tissues, and the spring is released so as to suit the hole size and follow its shape. The effect produced by the microsurgical fixing device on tissues can be controlled by appropriately selecting the magnitude of the angles at the bases of cone frustums, defined by the springs. The permissible effect produced on tissues for differently stiff springs is attained, as a rule, when the magnitude of the base angle of cone frustum is not in excess of 45 degrees.

Figure 7:
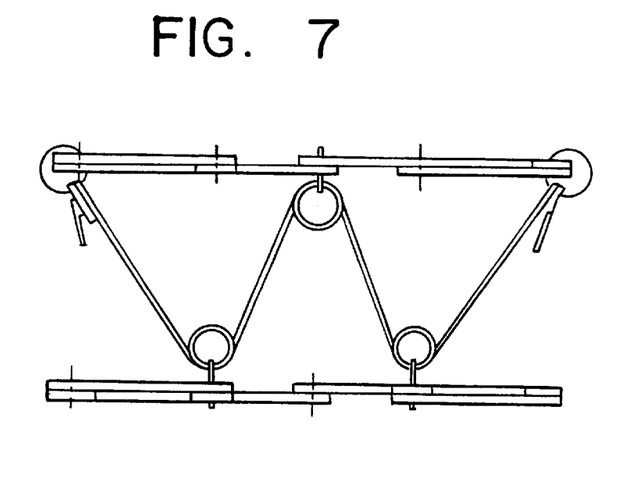
FIG. 7 illustrates the microsurgical fixing device comprising three springs, according to the invention.

In some alternative embodiments of the microsurgical fixing device use may be made of three or more springs joined successively together. An embodiment of the microsurgical fixing device with three springs is present in FIG. 7. This embodiment renders the fixing device positionable in intricately shaped body cavities.

A patch 6 can be affixed to one of the springs, using one of the commonly known techniques, e.g., by sewing on spring turns; also two patches can be held to two springs, thus providing closure of a hole in tissues on both sides (FIGS. 11–14).

Figure 5:
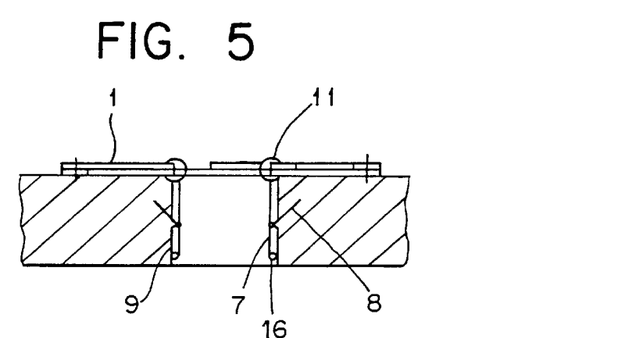
FIGS. 5 and 6 display a sectional view of the microsurgical fixing device while positioned on tissues, comprising one spring and retainers connected thereto through the various joining members, according to the invention.
Figure 6:
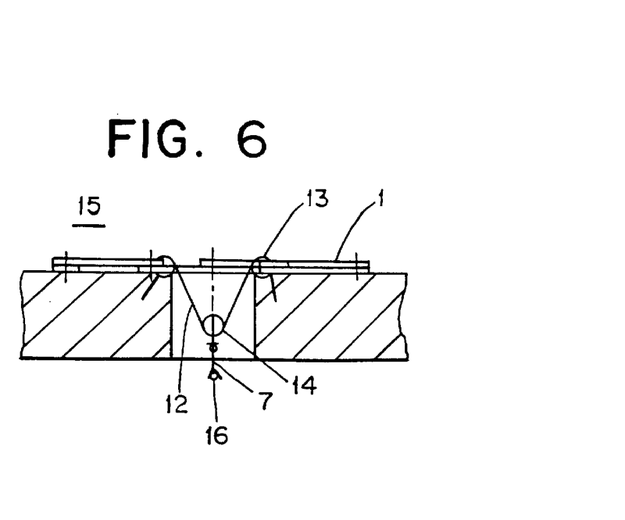

In another embodiment of the device a single spring is used, provided with retainers (FIGS. 5 and 6).

Used as said retainers may be any heretofore known fasteners capable of fixing, in combination with the spring properties, the microsurgical fixing device in every particular case of its use.

Each retainer may appear as an elastic bar 7 having at least one hook 8 fitted thereon through, e.g., a sleeve 9. When the sleeve is movable, the retainer bar is provided with locking shoulders which can be formed by bents 10 and projections or recesses of the retainer bar. To provide fixing of the device on tissues, in some particular embodiments thereof, the ends of the retainer hooks are oriented towards the spring as shown in FIG. 5.

To provide reversible spring compression in the cylindrical interior space of the positioning unit, the spring 1 is connected to the retainers 7 through joining members which may appear either as a ring 11 made up of one or more spring turns, or as a symmetrically curved clip 12 having a back and two legs provided with rings 13 at their ends. The clip back may have a spring turn 14. The retainer may be joined to the ring or the clip back either rigidly or movably, using the hole or ring at the retainer end.

Each joining member may have a further hook 15. The free end of the retainer bar is adapted to join the positioning unit through, e.g., a ring 16, a hole, a closed loop, a projection, or recesses.

When the spring is applied to the tissue with the greater base of the cone frustum and is fixed on said tissue with the aid of microsurgical retainers, the spring acquires the shape of a flat ring and proves to be in a slightly loaded state, whereby the device is fixed on tissues more reliably.

Figure 8:
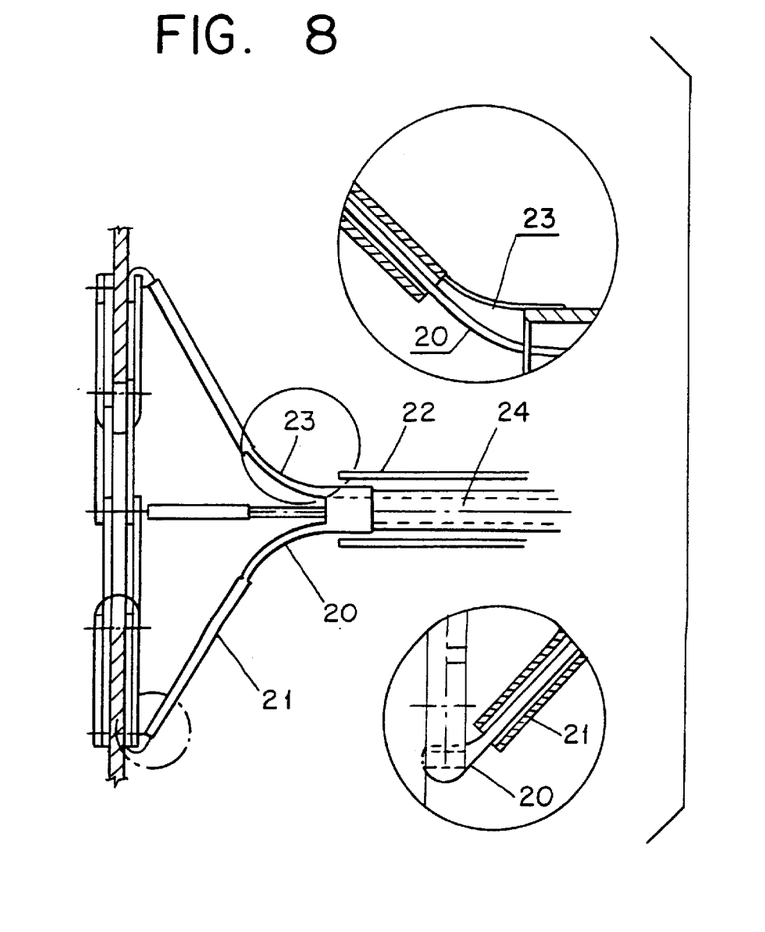
FIGS. 8 and 9 show the microsurgical fixing devices joined with the manipulation pusher, with the various embodiments of the microsurgical fixing device and of the manipulation pusher, according to the invention.

The proposed microsurgical fixing device with or without prosthetic appliance fixed therein is positioned using a positioning unit (FIG. 10) which comprises a transporting tube 17 provided with a butt-end joint 18 for separably joining with a cylinder-shaped sleeve 19 having its inside diameter equal to that of the transporting tube, and a positioning manipulation pusher. The positioning manipulation pusher comprises a tie-member 20 in an amount equal to that of the apices of spring zigzags, or that of the retainers of the microsurgical fixing device. Each tie-member is movable with regard to its respective slideway, in particular, as shown in FIG. 8, inside its own slideway 21 appearing, e.g., as a small tube. The slideways of the tie-members, according to the embodiment shown in the drawings, are spaced apart equidistantly and secured along the circumference of a cylindrical coupling 22. As shown in FIG. 8, the slideway is secured on the coupling through an elastic bar 23 one of whose ends is rigidly connected to the coupling 22, while the opposite end is bent out through a maximum angle of 90 degrees with respect to the axis of the manipulation pusher so that the joining bar is arc-shaped. The bend of the joining bar may be provided with a spring turn. When the slideways are secured on the coupling as described above, they may appear as small rigid tubes or bars with bent-out rings at their ends.

The coupling 22 may be connected to the distal end of a guide-catheter 24 through which the tie-members 20 are passed so that their ends 20 extend therefrom. A clamping fixture 25 is held to the guide-catheter so as to adjust the tie-members for length and tension. The clamping fixture may be shaped as, e.g., a collet clamp, spring lock, etc.

Figure 9:
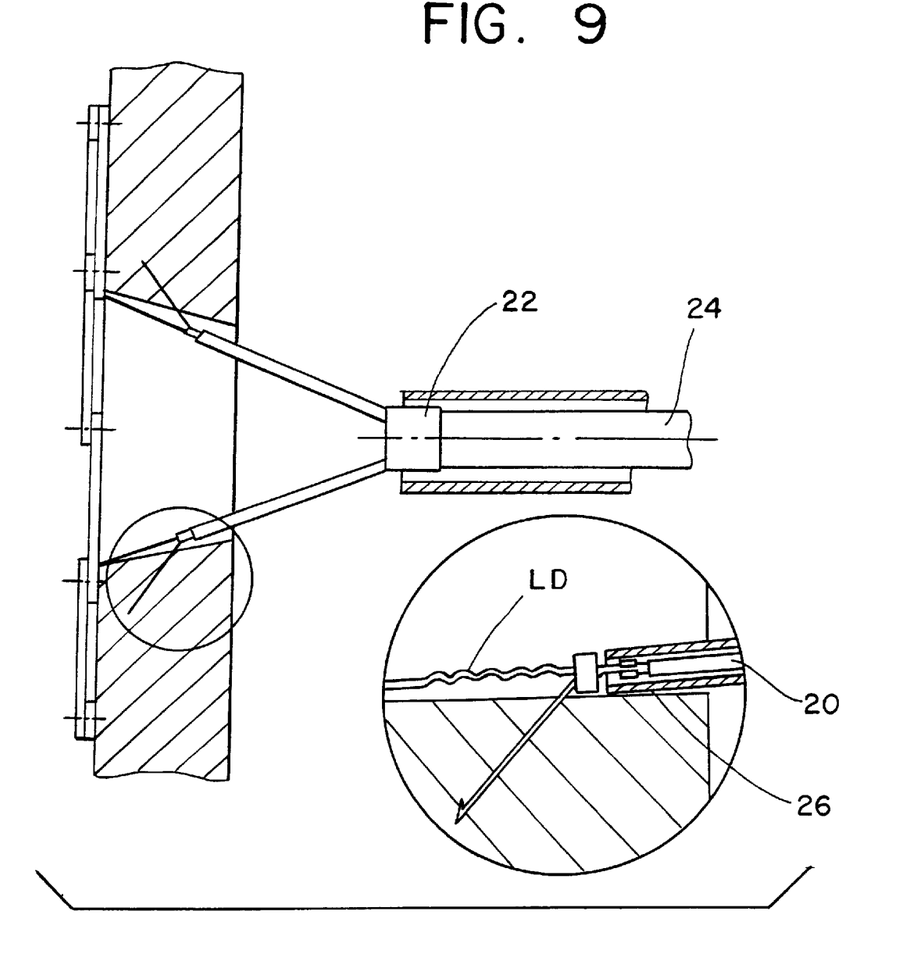

The tie-members 20 of the manipulation pusher may be either flexible and appear as a loop of a flexible cord, a string, or a monofilament or elastic and appear as elastic bars. According to some embodiments of the present invention, the ends of the elastic bars are bent out through a maximum angle of 90 degrees with respect to the axis of the manipulation pusher so that the bars are arc-shaped and the working ends are provided either with hooks 26, or projections, or recesses. In a specific embodiment of the manipulation pusher the tie-members running inside the guide-catheter are joined together.

In one of the embodiments of the manipulation pusher the coupling may be held to the proximal end of the guide-catheter through an articulated joint so as to incline either side from the axis of the manipulation pusher and to move axially relative thereto. The slideways are accommodated inside the guide-catheter and extend beyond its distal end.

An additional safeguarding tube may be fitted over the guide-catheter coaxially and movably with respect thereto, said tube being adapted to accommodate the retainer portions carrying hooks with a view to preventing the hooks against premature catching the surrounding tissues during positioning manipulations.

A wide variety of construction embodiments of the proposed microsurgical fixing device is due to diversity of specific conditions for its application. Except for minor differences, positioning of each of the proposed microsurgical fixing devices is based on a single operational concept which can be presented with reference to positioning a fixing device comprising two springs appearing as cone frustums put together with their greater bases, or comprising two springs appearing as flat rings. In this case the springs of the microsurgical fixing device are connected to those zigzag apices which are disposed on the circles of lesser bases of cone frustums, or on the lesser circles of rings. This modification of the fixing device provides for its use in fixing the edges of holes in tissues, or as the joining member of a prosthetic appliance, e.g., a patch used for closing a defect or lesion of the wall of an organ. The proposed microsurgical fixing device can be positioned, taking account of its springy properties and ability to self-locking, using the manipulation pusher provided with flexible tie-members and low-elasticity slideways.

Preparatory to positioning the microsurgical fixing device, the size and shape of the hole and the thickness of the wall tissue are assessed and the microsurgical fixing device having appropriate parameters and technical characteristics is selected. Account should be made of the fact that a microsurgical fixing device positioned in a hole is capable, due to its springy properties, of sustaining elastic deformation in order to suit the size and shape of the hole. However, when the diameter of the inside circle established by the microsurgical fixing device is much in excess of the hole size, the pressure exerted by the device on the surrounding tissues proves to be excessive, whereby crimps may result on the fixed prosthetic appliance, such as a patch. When the hole size exceeds the diameter of the inside circle of the microsurgical fixing device and approximates the diameter of the outside circle thereof, a gap may occur and, under certain conditions, the microsurgical fixing device may fall out of the hole, which is quite inadmissible. Therefore correct positioning and reliable locking of the microsurgical fixing device must be under constant control either visually by direct observation or with the aid of commonly known special equipment. When the device is found to have been mispositioned or its size is inconsistent with that of the hole to be closed, it must be withdrawn and replaced with a suitable one.

Figure 10:
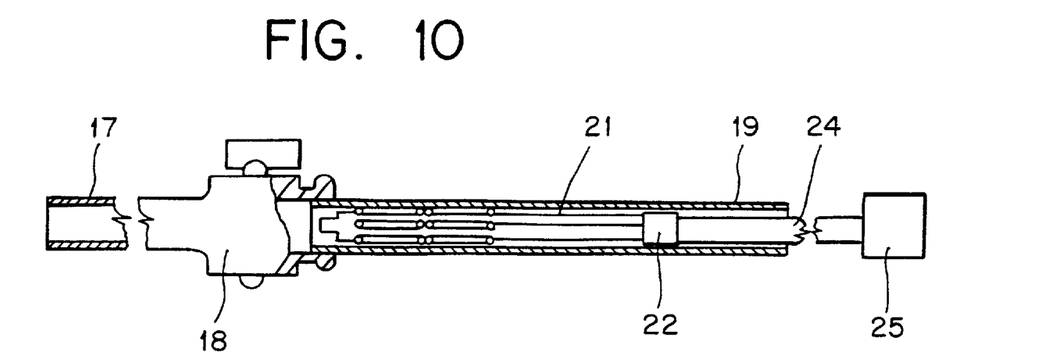
FIG. 10 illustrates the positioning unit carrying the microsurgical fixing device joined together with the manipulation pusher and accommodated in a cylinder-shaped sleeve, according to the invention.
Figure 11:
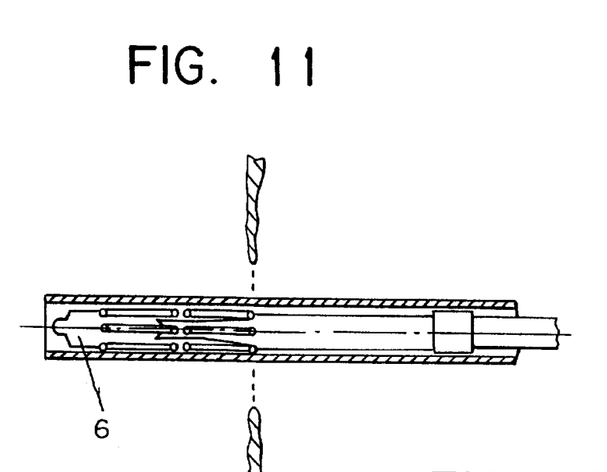
FIGS. 11 through 14 illustrate the steps of the positioning procedure of the microsurgical fixing device on a tissue, using the manipulation pusher.

While preparing the microsurgical fixing device for positioning, the positioning manipulation pusher is put inside the cylinder-shaped sleeve 19 coaxially and movably with respect thereto. The tie-members 20 and their slideways 21 are extended beyond the cylinder-shaped sleeve 19, and the ends of the tie-members, beyond the ends of the slideways. Then the microsurgical fixing device is joined with the manipulation pusher, establishing a loop from each tie-member, and each loop of each tie-member is connected to a respective free zigzag apex on one of the springs of the microsurgical fixing device. The both ends of each tie-member are passed inside its respective slideway, and the ends of all tie-members are passed inside the coupling and the guide-catheter, whereupon an equal length of each tie-member is measured out beyond the latter and all the tie-members are secured in the clamping fixture. While keeping the guide-catheter 24, one should apply an axial force to all the tie-members at a time so as to tension them until the zigzag apices bear up against the ends of the slideways of the tie-members, whereby the microsurgical fixing device gets secured rigidly on the manipulation pusher. While in this position the tie-members are fixed stationary relative to the guide-catheter 24 with the aid of the clamping fixture.

Thus, the axes of symmetry of the joined-together microsurgical fixing device and manipulation pusher appear to be aligned, which enables one to compress, pull through the cylinder-shaped sleeve, and arrange the microsurgical fixing device together with the prosthetic appliance (patch) secured thereon, inside said cylinder-shaped sleeve, by merely effecting an axial movement of the manipulation pusher with respect to the cylinder-shaped sleeve 19. Whenever necessary, the microsurgical fixing device can be released from the cylinder-shaped sleeve by applying an axial force to the fixing device to move it relative to said sleeve, with the result that the fixing device is self-released until assuming its original shape, thereby spreading the prosthetic appliance (patch) fixed thereto. The manipulations mentioned above can be repeated many times without inflicting any damage to the microsurgical fixing device. While being arranged inside the cylinder-shaped sleeve for transportation, the fixing device and the manipulation pusher held together interact as an integral unit. When actuated by the end of the cylinder-shaped sleeve, the fixing device experiences, either directly or through tie-members and slideways, a compound power action having a variable vector resulting in consecutive compression of each of the fixing device springs which when compressed change their shape consecutively from flat to conical, then to cylindrical structure. After having been released from the cylindrical interior space of the positioning unit, the fixing device is self-spread to change its shape in the reverse order. This property of the fixing device is used when positioning it in a hole of tissue. The way for transporting the fixing device may somewhat vary depending on the location and accessibility of the hole in tissue to be closed. When the conditions permit it, the fixing device can be positioned directly from the cylinder-shaped sleeve 19 without using the transporting tube 17. Otherwise the fixing device is transported along the transporting tube 17 whose distal end is preliminarily positioned at a required place using known techniques. In this case the cylinder-shaped sleeve accommodating the fixing device is joined together with the proximal end of the transporting tube, whereupon an axial force is applied to the manipulation pusher in order to displace the fixing device from the cylinder-shaped sleeve along the transporting tube to its distal end.

Figure 12:
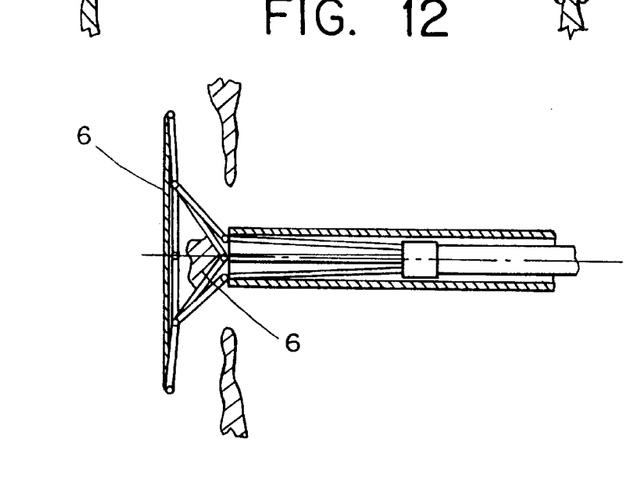
Figure 13:
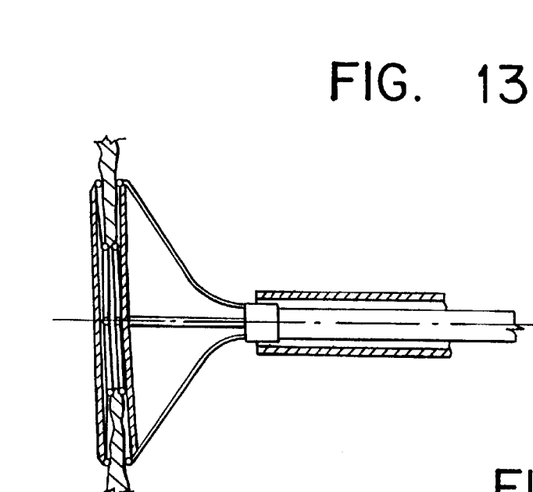
Figure 14:
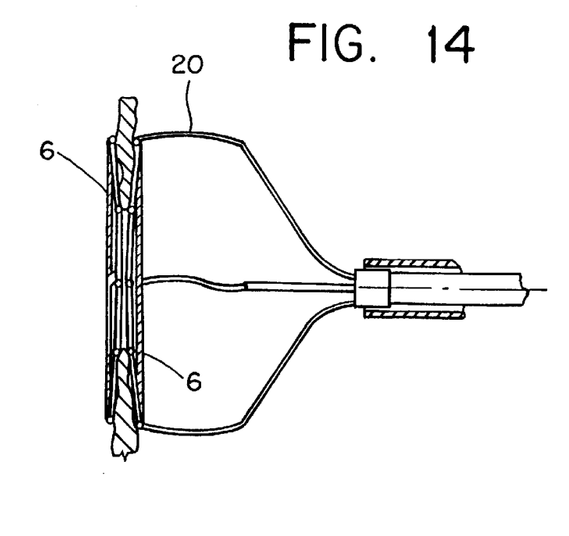

Further on, while monitoring the position assumed by the distal end of the transporting tube, the end of which should be passed through the hole beyond the wall of the organ (FIG. 11), one should extend the manipulation pusher till a position in which the slideways are directly at the outlet of the transporting tube and the fixing device gets partly released beyond the hole in tissue (FIG. 12). The distal spring of the fixing device (which is disjoined from the manipulation pusher) is released to assume a flat shape, and the patch held thereto is spread completely. The proximal spring of the fixing device (which is joined together with the manipulation pusher) is released partially to assume a conical shape due to the fact that the apices of the spring zigzags held to the manipulation pusher are pulled up to the end of the transporting tube. Then an axial force is applied to simultaneously displace the transporting tube and the positioning manipulation pusher, thereby introducing the self-centering fixing device into the hole in tissue. The fact that the size of the fixing device is selected correctly is additionally judged against the degree of resistance offered to the device and its resultant elastic deformation. Once the distal spring of the fixing device gets forced against one side of the hole face, and the places at which the springs are joined together are at the level of the hole edges, with a fixed position of the positioning manipulation, an axial force is applied to the transporting tube 17 to shift the latter and to release the slideways 21 of the tie-members. As a result, the proximal spring of the fixing device experiencing a weakened action thereon, assumes the initial shape and is fixed at the hole edges so that the springs are located on one and the other sides of the hole face (FIG. 13). Then a fixed restriction of the length of tie-members that has been used for compression, transporting, and positioning of the fixing device is eliminated. When pulling at the guide-catheter the length of the portions of tie-members between the apices of spring zigzags and the ends of the slideways increases (FIG. 14). Next the fixing device is further checked for correct positioning, since untensioned tie-members virtually exert no action, due to their low elasticity, on the fixing device, and its stable position depends on how reliable the device is held in the hole of tissue. Once the position of the fixing device has been considered correct, the tie-members are disjoined from the apices of the spring zigzags by pulling each tie-member at one of its ends. Finally, the positioning unit is withdrawn.

The fixing device can be withdrawn and replaced without being damaged or inflicting injury to the tissues surrounding the hole. The fixing device can be positioned in a somewhat different way. To this end, the fixing device is completely released from the transporting tube and spread till the initial position beyond the hole. Then a force is applied to the manipulation pusher to pull it into the hole. As a result, the slideways are brought together under the pressure exerted by the hole edges, thus compressing the fixing device spring held thereto, which spring is free to pass, in a compressed state, into the hole. Once the places of joining the springs together get at the level of the hole edges, the force compressing the proximal spring disappears so that the spring gets released to hold the fixing device in position.

The microsurgical fixing devices comprising more than two springs are positioned in the same way.

A microsurgical fixing device comprising a single spring and retainers is positioned using the same components and in the same sequence but with allowance for its construction features stemming from the fact that the spring used therein is intended for carrying a prosthetic appliance (patch) and for retaining the fixing device by the wall of tissue from one side of the hole, while final fixing of the device is carried out not until the released spring is forced against the tissue and the hooks of the retainers penetrate into the bulk of the tissue. Account is therein taken of the fact that the retainers are incapable of self-locking and that a force is required for their securing on the tissue, said force being built up by virtue of elastic properties of the positioning manipulation pusher. Having regard to the fact, a microsurgical fixing device comprising a single spring and retainers is positioned using a manipulation pusher having either tie-members made from elastic bars or flexible tie-members in combination with elastic slideways deflected to a required angle from the axis of the fixing device. With the correctly selected size of the microsurgical fixing device, any of the preselected construction embodiments of the manipulation pusher should bring the ends of the retainers held thereto, elastically apart a distance exceeding the radius of the hole (the orifice or opening of a tubular organ) into which the microsurgical fixing device is to be positioned.

Prior to placing the fixing device in the cylinder-shaped sleeve the retainer is secured on the manipulation pusher, when the manipulation pusher comprises flexible tie-members they are joined through a loop passed through the hole or ring at the retainer end; when the tie-members appear as elastic bars they are joined, through their end hooks, projections, or recesses, to the rings, holes, or recesses at the free ends of retainers. With the tie-members appearing as elastic bars, the places of their joining with the retainers are displaced inwards the slideways shaped as small tubes, and the tie-members are fixed in that position with respect to the guide-catheter. Once having been joined to the retainers of the fixing device, flexible tie-members are tensioned until the ends of the slideways bear against the ends of the retainer bars, or against the stationary fixed sleeves of the retainer hooks, and are also fixed in position with respect to the guide-catheter.

Once the transporting tube 17 carrying the cylinder-shaped sleeve 19 has been passed through the hole, the spring is freed from said tube and is released to assume its original shape. Then a force is applied to the manipulation pusher to pull the spring into the hole. Once the retainers have been arranged in the hole, the safeguarding tube (if any) is shifted to release the retainer hooks 8 and the tie-members 20 with the slideways 21, with the result that the spreading-apart action of the tie-members and slideways centers the fixing device and forces the retainers against the hole edges, whereby said edges are fixed in position with the aid of the hooks. In cases where use is made of retainers comprising hooks mounted on movable sleeves, they are moved using the manipulation pusher comprising tie-members made from elastic bars by virtue of longitudinal motion of the tie-members relative to the slideways. Once the fixing device has been held in position and released from the manipulation pusher, the positioning unit is withdrawn. When the microsurgical fixing device is found to have been mispositioned or held in place unreliably, it can be withdrawn from the hole and removed by being re-placed in the transporting tube 17.

INDUSTRIAL APPLICABILITY

Practical use of the proposed invention makes it possible to materially extend the functional capabilities of microsurgical fixing devices and to attain better results of operative interferences.

What is claimed is:

1. A microsurgical fixing device, comprising a spring appearing as a flexible Z-shaped bar that forms a closed loop, CHARACTERIZED in that it further comprises at least one spring appearing also as a flexible Z-shaped bar, each of said springs being so arranged that its opposing apices are disposed along the perimeters of the bases of a cone frustum or along concentric circles that form a flat ring, while the apices of zigzags of said Z-shaped bar in each spring located on the same base of the cone frustum or along the same ring circle are joined together with the apices of zigzags of a next spring which are also arranged on the same base of the cone frustum or along the same ring circle through joining members so as to provide ability for said springs to be compressed reversibly, and the apices of zigzags not joined together are adapted to receive the actuating members of a positioning unit.

2. A microsurgical fixing device as set forth in claim 1, CHARACTERIZED in that it comprises two springs, each appearing as a cone frustum, while joined together are the apices of zigzags located on the greater bases of the cone frustums formed by each of the springs.

3. A microsurgical fixing device as set forth in claim 1, CHARACTERIZED in that it comprises two springs, each appearing as a cone frustum, while joined together are the apices of zigzags located on the lesser bases of the cone frustums formed by each of the springs.

4. A microsurgical fixing device as set forth in claim 3, CHARACTERIZED in that the springs are put together with the greater bases of the cone frustums.

5. A microsurgical fixing device as set forth in claim 4, CHARACTERIZED in that the diameters of the greater bases of the cone frustums formed by each spring are unequal.

6. A microsurgical fixing device as set forth in claim 4, CHARACTERIZED in that angles at the greater bases of the cone frustums formed by each of the springs, are not in excess of 45 degrees.

7. A microsurgical fixing device as set forth in claim 1, CHARACTERIZED in that at least one spring turn is provided at each zigzag apex.

8. A microsurgical fixing device as set forth in claim 1, CHARACTERIZED in that the bar from which the spring is manufactured is made of wire having its various portions differing in shape and cross-sectional area.

9. A microsurgical fixing device as set forth in claim 1, CHARACTERIZED in that each joining member appears as a bracing ring whose size is selected so that the device may be placed in the positioning unit.

10. A microsurgical fixing device as set forth in claim 9, CHARACTERIZED in that the bracing ring appears as at least single spring turn.

11. A microsurgical fixing device as set forth in claim 1, CHARACTERIZED in that each joining member appears as a flexible bar provided with rings or holes at its ends, the size of said rings being so selected that the device may be placed in the positioning unit.

12. A microsurgical fixing device as set forth in claim 1, CHARACTERIZED in that each joining member appears as a tension spring provided with rings at its ends, the size of said rings being so selected that the device may be placed in the positioning unit.

13. A microsurgical fixing device, comprising a spring appearing as a flexible Z-shaped bar that forms a closed loop, said spring being so arranged that its opposing apices are arranged along the perimeters of the bases of a cone frustum or along concentric circles which form a flat ring, while all the apices of zigzags that are located on one of the bases of the cone frustum or on one of the circles of said flat ring are provided with retainers, each appearing as a flexible bar and has at least one hook; each retainer is movably connected, through the joining members, to at least one open of zigzags so as to provide reversible compression of the spring; all the retainers are situated on the same side of the spring and the free ends of the retainer bars are adapted to receive the actuating members of the positioning unit.

14. A microsurgical fixing device as set forth in claim 13, CHARACTERIZED in that the angle at the greater base of a cone frustum defined by the spring, is not in excess of 45 degrees.

15. A microsurgical fixing device as set forth in claim 13, CHARACTERIZED in that the hooks of all the retainers are oriented away from the spring axis.

16. A microsurgical fixing device as set forth in claim 13, CHARACTERIZED in that at least one spring turn is provided at each of the zigzag apices.

17. A microsurgical fixing device as set forth in claim 13, CHARACTERIZED in that the bar from which the spring is manufactured, is made of wire having its various portions differing in shape and cross-sectional area and is provided with hooks, or knurling, or spring turns.

18. A microsurgical fixing device as set forth in claim 13, CHARACTERIZED in that a hole or ring is provided at the end of each retainer opposite to the free end thereof for movably connecting the retainer to the joining member.

19. A microsurgical fixing device as set forth in claim 13, CHARACTERIZED in that each joining member connecting the retainer to one zigzag apex appears as at least one of a closed ring or a ring with at least one spring turn, the size of said rings being so selected that the device may be placed in the positioning unit.

20. A microsurgical fixing device as set forth in claim 13, CHARACTERIZED in that each joining member is made from a flexible bar and appears as a symmetrically curved clip having a back and two legs provided with rings at their ends and connected to two adjacent zigzag apices, while the clip back is connected to the retainer.

21. A microsurgical fixing device as set forth in claim 20, CHARACTERIZED in that the clip back has at least one spring turn movably connected to the ring or hole provided at the retainer bar end opposite to the free end thereof.

22. A microsurgical fixing device as set forth in claim 13, CHARACTERIZED in that each retainer has the free end of its bar adapted to receive the actuating members of the positioning unit, is provided wit at least one of a hole, or ring, or projection, or recess.

23. A microsurgical fixing device as set forth in claim 13, CHARACTERIZED in that the retainer hook is fitted on a sleeve fixed in position on the retainer bar.

24. A microsurgical fixing device as set forth in claim 13, CHARACTERIZED in that the retainer hook is provided on a sleeve which is movable over the retainer bar from the initial to the fixing position.

25. A microsurgical fixing device as set forth in claim 13 CHARACTERIZED in that each joining member has at least one further hook.

26. A manipulation pusher, comprising a number of tie-members, each being adapted to join to the components of the present microsurgical device, CHARACTERIZED in that it further comprises slideways in a number equal to that of tie-members, and a guide-catheter connected, through a coupling, to the slideways secured thereon; each tie-member is longitudinally movable inside the coupling and the guide-catheter with regard to its respective slideway, the length of each tie-member exceeds a total length of its respective slideway, the coupling, and the guide-catheter; the distal end of each slideway is adapted to interact with the component of the microsurgery device joined with the corresponding tie-member and the guide-catheter carries a clamping fixture adapted to fix the tie-members in position.

27. A manipulation pusher as set forth in claim 26, CHARACTERIZED in that each tie-member is made of a loop-shaped flexible cord or string.

28. A manipulation pusher as set forth in claim 26, CHARACTERIZED in that the tie-members appear as flexible bars provided with hooks, or projections, or recesses at the ends thereof which deflect at a maximum angle of 90 degrees with respect to the axis of the manipulation pusher.

29. A manipulation pusher as set forth in claim 26, CHARACTERIZED in that the slideways appear as small flexible tubes inside which tie-members are accommodated.

30. A manipulation pusher as set forth in claim 26, CHARACTERIZED in that the slideways appear as small tubes inside which tie-members are accommodated and which are secured on the coupling through flexible bars that deflect at a maximum angle of 90 degrees with respect to the axis of the manipulation pusher.

31. A manipulation pusher as set forth in claim 26, CHARACTERIZED in that the slideways are equal in length.

32. A manipulation pusher as set forth in claim 26, CHARACTERIZED in that the coupling is fitted at the distal end of the guide-catheter.

33. A manipulation pusher as set forth in claim 26, CHARACTERIZED in that the coupling is fitted at the proximal end of the guide-catheter through an articulated joint and the slideways are accommodated inside the guide-catheter and extend beyond its distal end.

34. A manipulation pusher as set forth in claim 26, CHARACTERIZED in that it further comprises a safeguarding tube fitted on the guide-catheter coaxially therewith.

* * * * *

UNITED STATES PATENT AND TRADEMARK OFFICE
CERTIFICATE OF CORRECTION

PATENT NO.   : 6,036,716
DATED        : March 14, 2000
INVENTOR(S)  : Kruchinin et al.

It is certified that error appears in the above-identified patent and that said Letters Patent is hereby corrected as shown below:

Title page,
Item [56], insert the following;

```
--        U.S. PATENT DOCUMENTS
5,104,399    4/14/92      Harrison M. Lazarus    623/1
4,710,192    12/1/87      Domingo S. Liotta      623/1

FOREIGN PATENT DOCUMENTS
SU 1,217,402 A    3/15/86     Russia
SU 1,821,176 A1   6/15/93     Russia
SU 1,318,235 A1   6/23/87     Russia
RU 2,000,814 C1   10/15/93    Russia
GB 2 200 848 A    8/17/98     Germany
GB 2 196 857 A    5/11/98     Germany --
```

Signed and Sealed this

Twenty-fourth Day of December, 2002

JAMES E. ROGAN
*Director of the United States Patent and Trademark Office*